United States Patent [19]
Talmi et al.

[11] Patent Number: 5,821,547
[45] Date of Patent: Oct. 13, 1998

[54] TEMPORAL FILTER USING INTERLINE CHARGED COUPLED DEVICE

[76] Inventors: Yair Talmi, 14 Russell Ct., New Town, Pa. 18940; Sam Khoo, 746 Valley Forge Ave., Laurenceville, N.J. 08648

[21] Appl. No.: 814,094

[22] Filed: Mar. 10, 1997

[51] Int. Cl.⁶ .................................................. G01J 1/58
[52] U.S. Cl. .................................. 250/458.1; 250/459.1; 250/461.2
[58] Field of Search .............................. 250/458.1, 459.1, 250/461.1, 461.2; 257/233; 377/62

[56] References Cited

U.S. PATENT DOCUMENTS

| | | |
|---|---|---|
| 5,005,085 | 4/1991 | Spies et al. . |
| 5,081,530 | 1/1992 | Medina . |
| 5,212,667 | 5/1993 | Tomlinson, Jr. et al. . |
| 5,514,887 | 5/1996 | Hokari ...................................... 257/233 |
| 5,585,652 | 12/1996 | Kamasz et al. . |

*Primary Examiner*—Edward P. Westin
*Assistant Examiner*—Richard Hanig
*Attorney, Agent, or Firm*—Kaplan & Gilman, LLP

[57] ABSTRACT

An Interline charge coupled device is utilized to capture events during a short duration of time. The Interline charge coupled device is connected to a controller which causes charge to begin being accumulating at the beginning of the time window of interest, and shifts the charge underneath the shielded portion of the Interline charge coupled device at the end of such time. Various applications including spectroscopy and imaging are disclosed as well.

17 Claims, 4 Drawing Sheets

TEMPORAL FILTER USING INTERLINE CHARGED COUPLED DEVICE

TECHNICAL FIELD

This invention relates to Interline charged coupled devices, and more particularly, to an improved use of an Interline charge coupled device which permits the capturing of relatively short duration light events in the presence of continuous background noise, continuous ambient illumination, and/or other undesirable signals with relatively long duration compared to the desired signal.

DESCRIPTION OF THE PRIOR ART

Charge coupled devices, including Interline charge coupled devices, comprise an array of elements (i.e.; photodiodes) for capturing light energy. Charge coupled devices and Interline charge coupled devices have been well known in the optics industry for many years and are presently in mass production by numerous companies. Eastman Kodak Company of Rochester, N.Y., for example, manufactures a wide variety of charge coupled devices which are typically purchased by original equipment manufacturers and integrated into other apparatus made available to the public or to the scientific research community. For example, typical consumer video cameras comprise Interline charge coupled devices. Charge coupled devices are also utilized in a variety of scientific and medical applications.

FIG. 1 shows a conceptual representation of an Interline charge coupled device 101 comprising 648 rows×484 columns of photodiodes. Each photodiode is used to represent one element (i.e.; pixel). The arrangement of FIG. 1 also includes, within the active area 105, numerous columns of shielded Vertical CCD shift registers indicated conceptually as 102. Light shielded dark reference rows and columns 103 surround the active area 105.

In operation, an electronic representation of an image is formed when incident photons falling on the sensor plane create electron-hole pairs within the individual silicon photodiodes. These photoelectrons are collected locally by the formation of potential wells at each photosite. Below photodiode saturation, the number of photoelectrons collected at each pixel is linearly dependant upon light level and exposure time and nonlinearly dependant upon wavelength. When the photodiode's charge capacity is reached, excess electrons may be discharged into the substrate.

The accumulated or integrated charge from each photodiode is transported to the output by first transferring it under the vertical shielded CCD registers 102. Once the charge is contained in the vertical shielded CCD registers 102, it is transferred out line by line (i.e; row by row) to horizontal register 106. Each row is read out through a preamplifier 104 on a pixel by pixel basis.

Although the device described with respect to FIG. 1 has an Interline structure, CCD devices without any Interline structure (i.e.; no shielded vertical registers) are also widely utilized. One such application of a charge coupled device without an Interline structure is in conjunction with an image intensifier. An image intensifier includes a small window upon which light impinges. A photon image incident on the window is transformed into a corresponding but greatly amplified electronic signal, which is then turned back into a photon image and is incident upon a CCD. The end result is that even the faintest image is sufficiently amplified to overcome the inherent noise of the CCD.

FIG. 2 depicts a block diagram of a side view of an arrangement including an intensified charge coupled device. The computer 210 and controller 208 work in conjunction to cause an excitation signal from source 209, and to cause a gating pulse to be placed upon line 211 at the appropriate time.

As shown in FIG. 2, light 20G from source 209 impinges upon intensifier 205 and is transferred through to charge coupled device 207 only when intensifier 205 is subjected to a gating pulse via electrical connection 211. By precisely applying a gate pulse of a predetermined duration (pulse width) and delay time with respect to a reference trigger pulse on line 212, the image intensifier, and therefore the Intensified CCD device, can be activated at the exact time required to capture an image or a spectrum. It is well known in the art that such intensifiers can permit time windows of the microsecond or even the nanosecond range.

There are numerous applications for the foregoing technique, all of which require the optical capture of a relatively short event of light. For example, in Laser Induced Breakdown Spectroscopy (LIBS), a laser is utilized to cause breakdown of subject molecules, and the emitted spectrum is captured and studied. The spectrum of interest is only emitted for a few microseconds, making the timing of the camera capturing the event is critical. Another application involves exciting a sample of biological tissue with laser energy. The sample responds to the excitation by emitting light energy. Again, the light energy is emitted for a relatively short time.

All of the applications have the common issue that if the charge coupled device is exposed for a time which is relatively long when compared with the event of interest, then the accumulated charge will be almost entirely the result of extraneous sources (e.g.; continuous ambient light) and not of the event of interest. Accordingly, the event of interest will be lost.

The arrangement shown in FIG. 2 permits a relatively short duration light response to be captured by a charge coupled device through the use of an intensifier. While this prior art arrangement is acceptable in that it prevents the event of interest from being lost in the background signal, there are several drawbacks. First, the intensifier is quite expensive, typically making the cost of such a system on the order of thousands of dollars. Second, the resolution of the intensifier is poor compared to that of the CCD, and thus, the signal gets degraded as it passes through the intensifier. Accordingly, the signal ultimately captured by the charge coupled device is different from the actual response of the sample. Third, the quantum efficiency of the intensifier is poor compared to that of the CCD. Fourth, intensifiers are subject to damage by excessive exposure to light, a phenomenon termed light shock. Fifth, the signal to noise ratio of many intensifiers is less than desirable. Finally, intensifiers have a limited lifespan of a few thousand hours, after which replacement is required. Nonetheless, the cost factor remains the single most problematic issue with the use of the intensifier based system shown and described with respect to FIG. 2 for wide spread applications.

In view of the above it can be appreciated that there exists a need in the art for a relatively inexpensive image recording system which can effectively capture very short duration events in the presence of unwanted illumination such as a constantly lit environment (i.e.; ambient light). The unwanted illumination must be minimized in order to prevent the charge coupled device from being filled with energy that is not indicative of the desired signal.

SUMMARY OF THE INVENTION

The above and other problems of the prior art are overcome in accordance with the present invention which relates to an apparatus and method for capturing relatively short duration events at precise times by utilizing the ability of an Interline charge coupled device to substantially instantaneously (e.g.; a few microseconds) transfer its charge underneath the shielded portions of the various matrix elements. Specifically, in accordance with the invention, an Interline charge coupled device is connected to a controller which can precisely control the time at which the Interline charge coupled device begins accumulating charge, as well as the time at which the charge is transferred underneath the shielded portion of the matrix elements. The time difference between the initiation of charge being accumulated and the transfer of charge under the shield is denoted the "sampling time".

The controller is arranged to cause, at a precisely controlled time, the event which is to be captured by the Interline charge coupled device camera. Thereafter, the controller is utilized to control the Interline charge coupled device to capture the event of interest and place it under the shielded portion.

In furtherance of the above objective, the controller causes excitation of the source, typically but not necessarily by activating a laser, and awaits the prescribed delay until the excitation signal causes a response. At the time the response begins, the controller causes the Interline charge coupled device to begin accumulating charge. The accumulated charge is thus a result of the response desired to be monitored.

After the window of time in which the event of interest occurs has elapsed, the controller causes the Interline charge coupled device to quickly shift the accumulated charge underneath the shielded portion of the Interline charge coupled device elements. Accordingly, only the light falling on the Interline charge coupled device during the event of interest is recorded.

Thus, to the extent that there is background continuous illumination, or other signals which are relatively long in duration but which, during the sampling time, have far less amplitude than the light event of interest, the adverse affect of such unwanted signals on the signal to noise ratio during the sampling time will be greatly reduced. It has been determined that the reduction will be enough so that the light event of interest will still be readily ascertainable.

In essence, the relatively small amount of background light accumulated during the sampling time of the induced florescent signal will cause very little distortion to the accuracy and precision of the image or spectra being recorded. Additionally, with regard to the stimulus, e.g., the laser causing the excitation, the controller may be arranged such that the Interline charge coupled device does not begin accumulating charge until after the stimulus optical signal is removed.

In additional embodiments, the technique can be utilized in conjunction with a spectrometer to perform spectroscopy, or in conjunction with other elements, e.g. lenses, to perform other imaging functions.

In a further enhanced embodiment, the repeatability of certain responses is advantageously utilized. Specifically, the desired response is stored under the shielded portion of the Interline charge coupled device, as previously described. However, rather than immediately shift out the desired response, the excitation signal is again applied, and a second response is captured and cumulatively stored under the shielded portion. The process may be repeated several times, after which the total charge stored under the shielded portion is shifted out for processing. This multiple capture and store technique improves signal to noise ratio and provides greater amplitude of the signal of interest.

DETAILED DESCRIPTION OF THE PREFERRED EMBODIMENT

Figure 1:
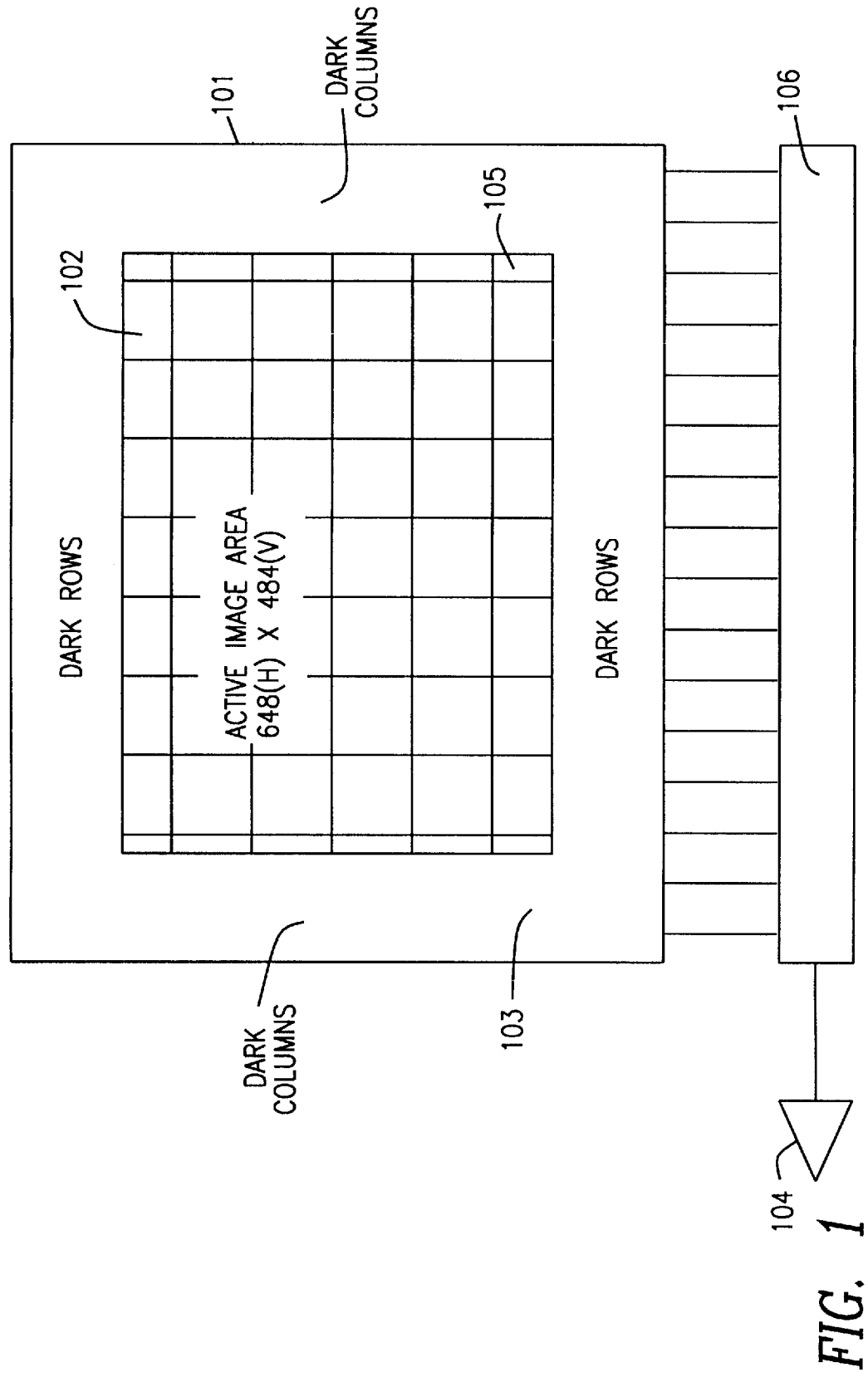
FIG. 1 is a depiction of a charge coupled device.
Figure 2:
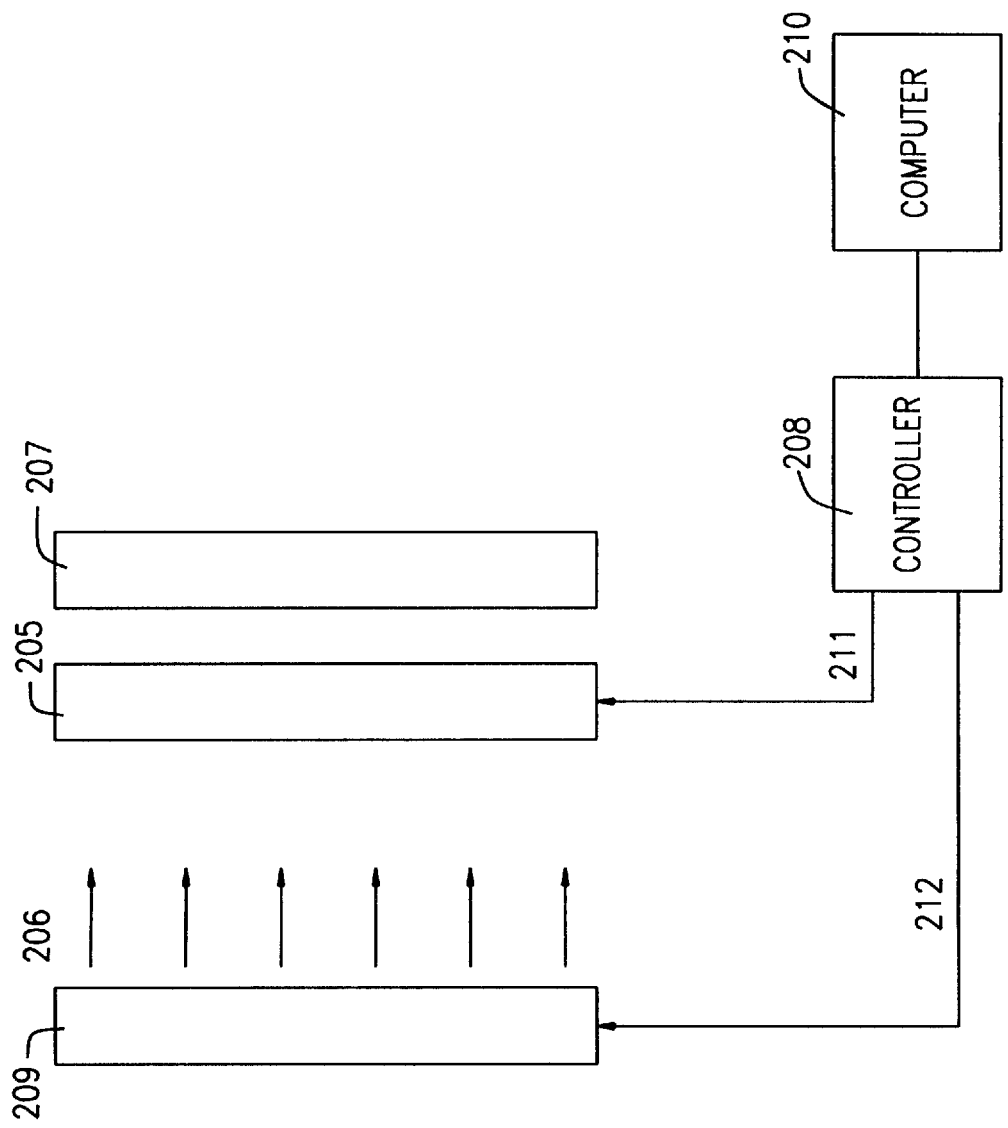
FIG. 2 shows a block diagram of a charge coupled device in conjunction with an intensifier for recording relatively short events.
Figure 3:
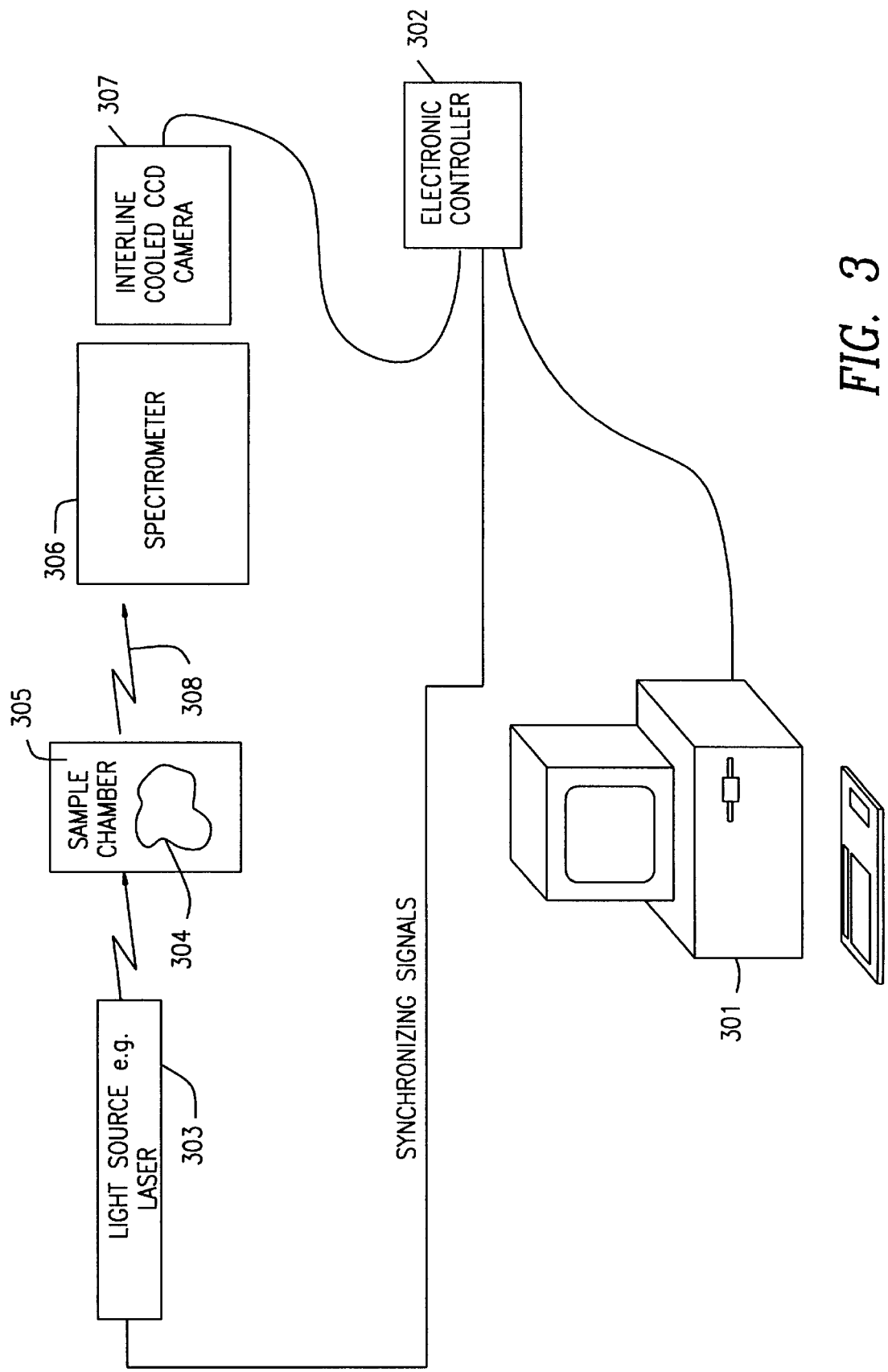
FIG. 3 depicts an exemplary arrangement for measuring the fluorescent response of biological tissue in accordance with the teachings of the present invention.

FIG. 3 shows a typical arrangement utilizing an Interline charge coupled device in conjunction with the techniques of the present invention in order to perform spectroscopy upon the fluorescent response of a sample after being excited by a laser source to cause laser induced florescence. It is noted that the utilization of the invention to perform spectroscopy on a fluorescent response of biological tissue is only exemplary and not for purposes of limitation of the invention.

The arrangement of FIG. 3 comprises a computer 301 coupled to controller circuit 302 which includes appropriate timing electronics. The controller is arranged to transmit synchronizing signals to a laser source 303 for exciting a sample 304 contained within a sample chamber 305. Also included in FIG. 3 is a spectrometer 306 and Interline charge coupled device camera 307. The camera may be optionally cooled for the purpose of reducing dark charge signal and its associated noise.

In operation, the computer 301 is programmed with appropriate software which is dependant upon the particular application. In the present example, the application is the measurement of the fluorescent response of a biological tissue sample excited with a laser. Appropriate software for causing and viewing such response is available from Princeton Instruments, Trenton, N.J., the assignee of the present patent application. The computer is arranged to cause controller 302 to excite the laser source 303 and thereby cause a response from sample 304. This technique has been utilized for decades by the assignee of the present application and the instrumentation used trademarked as OMA (optical multichannel analyzer), more then 24 years ago.

The spectrometer 306 is a conventional spectrometer available off the shelf and well known to those of ordinary skill in the art. The spectrometer performs a spatial frequency transform on the wavelength response signal 308. Accordingly, the spectrum falls upon Interline charge coupled device 307. Each column of the Interline CCD device samples the wavelength response at a different wavelength to reconstruct and simultaneously detect the complete spectral range of interest.

Controller 302 turns the Interline charge coupled device camera on to begin gathering charge at as close as possible to the moment that the response is expected to occur. For example, if the response occurs five microseconds after the laser source is activated, then the controller would trigger Interline charge coupled device camera 307 to begin gathering charge just five microseconds after the synchronizing signal is transmitted to laser source 303. At the end of the response period during which it is desired to gather the response information, controller 302 causes Interline charge coupled device camera 307 to shift the charge under the shielded portion of the Interline charge coupled device elements and thereby terminate the sampling period.

Figure 4:
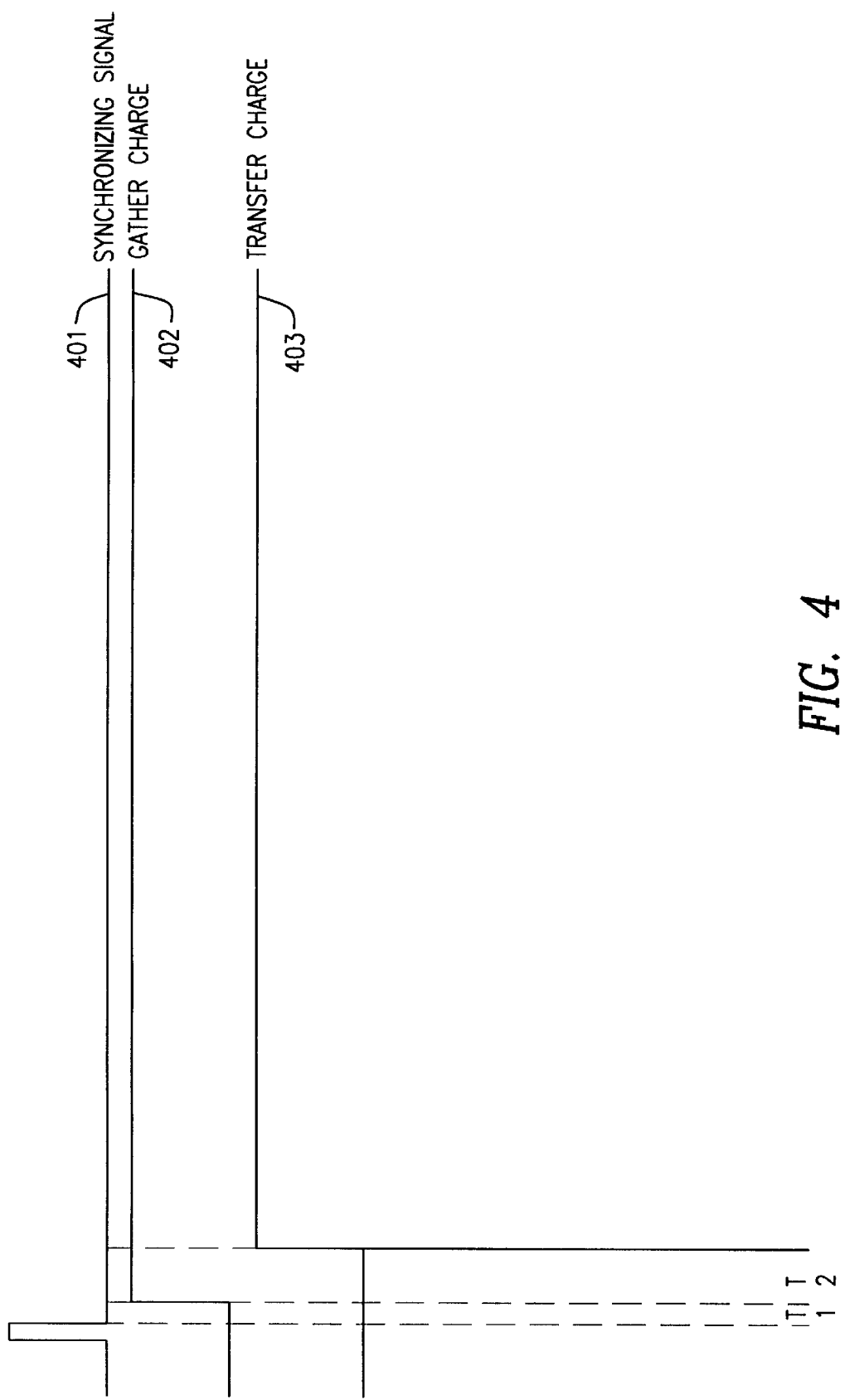
FIG. 4 shows a timing diagram for use in the operation of the arrangement of FIG. 3.

A timing diagram setting forth the above description is shown in conceptual form at FIG. 4. As previously indicated, synchronizing signal 401 causes the laser source 303 to emit its laser light which, after a known delay period of T1 as indicated in FIG. 4, causes the response to occur from sample 304. Accordingly, at the end of T1, gather charge signal 402 is sent by controller 302 to cause Interline charge coupled device camera 306 to begin gathering charge. At the end of the response period T2, the transfer charge signal 403 causes the charge to be shifted underneath the shielded portion of the Interline charge coupled device camera, thereby capturing substantially all of the light falling upon the Interline charge coupled device only during the period T2 of interest. While there is no temporal discrimination between the background signal the induced response, the effect of the background is greatly reduced by capturing signal only during the sampling time.

In an enhanced embodiment, the arrangement of FIG. 3 may be programmed to cause repetitive excitation of laser source 303 and repetitive and cumulative capturing of the fluorescent response from sample 304. Specifically, after the response is captured by Interline charge coupled device 307 and stored under the shielded portion thereof, the laser source 303 is again excited and a new response is stored under the shielded portion. Presuming the response is substantially identical each time the stimulus is applied, the cumulative effect of the signals being stored under the shielded portion of Interline charge coupled device 307 is to add the signal of interest while significantly reducing the noise from the background signal. Accordingly, signal to noise ratio increases, typically square root proportionally with respect to the number of consecutive accumulations. The computer software and/or controller may be readily configured to capture several cycles of response before the charge stored in the shielded portion of the Interline charge coupled device 307 is read out into computer 301 for processing and/or display.

It is noted that the prior art intensifier system allows events to be captured which are of the nanosecond order in terms of duration. The present device is limited to much longer durations. It will be clear to those of ordinary skill in this art that the minimum time duration which will be captured by the above device will be the time to transfer the charge from the unshielded to the shielded portion of the Interline charged coupled device. More particularly, if at the time the device starts gathering charge, it is immediately signalled to transfer its charge to the shielded portion (i.e.; T2 in FIG. 4 is zero), there will still be approximately several microseconds of charge accumulation since it takes at least that long to transfer the charge from the unshielded to the shielded portion. Nonetheless, in many medical and other scientific applications, there is no requirement to reach the nanosecond range and a microsecond event time is sufficient. Accordingly, the decreased cost and other benefits of the present system will more than justify replacing prior art intensifier based systems in certain applications.

Additionally, if fast Interline charge coupled devices become available in the future, then the present invention may be utilized to capture even shorter duration events. Such a system could directly compete with much more expensive intensifier based systems.

One application of the inventive system where cost is clearly a predominant factor is when a physician is examining an internal organ through a probe and notices a growth. The physician may desire to excite the growth with laser energy and measure the response (i.e.; laser induced florescence). The situation where a biological sample of tissue is being excited and the response measured could occur directly in a physician's office while the biological tissue is still attached to the human body. In such a situation, not only is the response present, but the charge coupled device is also subjected to continuous illumination, typically from high intensity incandescent light bulbs required for the physician to do the examination. Thus, the light detected by the CCD device elements would be predominantly from the ambient light required for the physician to do the examination. Therefore, the desired florescent or other response would be lost. By utilizing the present techniques, the Interline charge coupled device significantly reduces the unwanted energy, yet can be sold inexpensively enough such that every physician's office could be equipped with such a device.

It is understood that the above embodiments are only representative. Many other variations will be apparent to those of ordinary skill in this art. For example, the spectrometer 306 may be eliminated and replaced by various lens apparatus to perform any imaging function typically detected by CCDs, yet the technique of temporal discrimination of the present invention may still be utilized. Stimuli and samples other than those shown in FIG. 3 or described herein may be used. Additionally, in certain applications, the stimulus laser signal may be eliminated through a filter. Raman spectroscopy may be accomplished with the device as well.

These and other variations are intended to be covered by the claims appended hereto.

We claim:

1. A method of capturing a light signal response produced by a sample when subjected to a stimulus, said response comprising light energy occurring at a predetermined time after said stimulus and for a predetermined duration, said light energy impinging upon a surface, said method comprising the steps of:

applying said stimulus;

waiting a predetermined amount of time for said response to occur after said stimulus is applied;

initiating, immediately subsequent to said predetermined amount of time, the accumulation of energy on the surface, said energy accumulated being in response to, and deterministicaly related to, the amount of light energy impinging upon said surface; and transferring said accumulated energy to a surface which does not accumulate energy in response to light immediately after said duration.

2. The method of claim 1 wherein said step of accumulating comprises the steps of utilizing an Interline charge coupled device having a shielded and unshielded portion, and accumulating light energy on the unshielded portion of the Interline charge coupled device by converting said light energy to electrical energy; and said step of transferring comprises transferring the charge to the shielded portion of the Interline charge coupled device.

3. The method of claim 2 further comprising the step of passing said response through a spectrometer before said response reaches said Interline charged coupled device such that said light energy recorded on said Interline charged coupled device is light energy corresponding to a spectrum of said response.

4. The method of claim 3 wherein said step of applying a stimulus includes the step of exciting a sample of biological tissue with a laser beam.

5. The method of claim 3 wherein said duration is equal to the minimum amount of time required to transfer charge from said unshielded portion to said shielded portion.

6. Apparatus for capturing a response of a sample when said sample is subjected to a stimulus, said response occurring at a predetermined delay after said stimulus and comprising light energy, said apparatus comprising;

stimulus means for subjecting a sample to said stimulus, an Interline charge coupled device comprising an unshielded portion and a shielded portion, and positioned to capture said response; and timing means configured to (i) activate said stimulus, (ii) initiate capture of said response after said predetermined delay, and (iii) terminate capture of said response by facilitating transfer of charge from said unshielded to said shielded portion after said duration.

7. Apparatus of claim 6 further comprising a spectrometer for receiving said response at an input thereof and transmitting a spectrum of said response from an output of said spectrometer to said unshielded portion of said Interline charge coupled device.

8. A method of increasing the effectiveness of an Interline charge coupled device having a shielded portion and an unshielded portion comprising the steps of:

repetitively accumulating and transferring charge from said unshielded portion to said shielded portion such that charge from several such transfers accumulates in said shielded portion; and moving said charge out of said shielded portion after said several transfers.

9. The method of claim 8 further comprising the step of causing charge to be (i) accumulated during a response event of interest and (ii) transferred after said response event of interest.

10. The method of claim 3 wherein said step of applying includes the step of inserting a source of said stimulus into an orifice of a living body.

11. The method of claim 1 wherein said step of waiting comprises waiting long enough such that said stimulus is no longer present.

12. Apparatus of claim 6 wherein said timing means is configured to initiate capture of said response after a predetermined delay which is longer than the duration of the stimulus.

13. Apparatus for measuring a photo response of biological tissue, said response having a spectrum and a duration, said apparatus comprising:

a laser for causing a stimulus;

a spectrometer for receiving said response as an input thereof and for generating an output signal indicative of said spectrum;

an Interline charge coupled device arranged proximate to said spectrometer for receiving said output signal; and timing means arranged to facilitate the following events in sequence (i) activation of said laser to cause excitement of said biological tissue (ii) deactivation of said laser (iii) delay of x, where x is an amount of time required for said biological tissue to begin responding to said stimulus (iv) initiation of recording of said spectrum and (v) transfer of charge from an unshielded to a shielded portion of said Interline charge coupled device at the end of said duration.

14. Apparatus for inducing a response and for recording said response while discriminating the response from a continuously present signal, said response having a response time, said continuously present signal having substantially less amplitude during said response time than said response, said apparatus comprising:

laser means for exciting a sample;

means for exposing an unshielded portion of an Interline CCD to said response for a temporal duration substantially equal to said response time, said temporal duration beginning substantially simultaneously with said response; and means for transferring charge from the unshielded portion to the shielded portion of said CCD at the end of said temporal duration so that a contribution of charge in said shielded portion from said continuously present signal is negligible with respect to a contribution of charge from said response, thereby discriminating said response from said continuously present signal.

15. Apparatus of claim 14 further comprising means for providing ambient light as said continuously present signal.

16. Apparatus of claim 13 further including means for generating a Raman response.

17. Apparatus of claim 13 further including means for generating a fluorescent spectral response.

* * * * *